United States Patent
Blumberg (10) Patent No.: US 9,342,660 B1
(45) Date of Patent: May 17, 2016

(54) DETECTION OF CHEMICAL ANALYTES VIA OPTICAL CORRELATIONS

(75) Inventor: Girsh Blumberg, New Providence, NJ (US)

(73) Assignee: Alcatel Lucent, Boulogne-Billancourt (FR)

( * ) Notice: Subject to any disclaimer, the term of this patent is extended or adjusted under 35 U.S.C. 154(b) by 3071 days.

(21) Appl. No.: 11/584,452

(22) Filed: Oct. 20, 2006

(51) Int. Cl.
*G01N 33/48* (2006.01)
*G06F 19/00* (2011.01)
*G06G 7/58* (2006.01)

(52) U.S. Cl.
CPC ...................................... *G06F 19/70* (2013.01)

(58) Field of Classification Search
CPC ....................................................... G06F 19/70
See application file for complete search history.

(56) References Cited

U.S. PATENT DOCUMENTS 5,194,912 A * 3/1993 Batchelder et al. ........... 356/301
6,040,906 A * 3/2000 Harhay ......................... 356/301

OTHER PUBLICATIONS

G. E. Blumberg and L.A. Rebane, "Determination of multimode vibronic interaction parameters from low-temperature profiles of resonant scattering of light. Excitation of resonant scattering of light. $KBr:MnO_4^-$ crystal as example", Sov. Phys. JETP 67 (11) Nov. 1988, pp. 2293-2300.

* cited by examiner

*Primary Examiner* — Eric S DeJong
(74) *Attorney, Agent, or Firm* — Carl Bilicska; John F. McCabe (57) ABSTRACT

A method for detecting or identifying a chemical analyte includes measuring a nontrivial set of correlations between optical illumination wavelengths of a sample and emission wavelengths of the sample. The method includes comparing the measured set of correlations to a reference nontrivial set of correlations between optical illumination and emission wavelengths of a specific chemical analyte. The method also includes determining whether the specific chemical analyte is present in the sample based on a result of the comparing.

8 Claims, 6 Drawing Sheets

DETECTION OF CHEMICAL ANALYTES VIA OPTICAL CORRELATIONS

BACKGROUND

1. Technical Field

The invention relates to apparatus and methods for detecting chemical analytes.

2. Discussion of the Related Art

In many contexts, it is desirable to have techniques for accurately identifying atomic and molecule species. Spectroscopy has been an important tool for accurately identifying atomic and molecular species. A spectrograph may show bright emission lines or dark absorption lines. An emission line spectrum shows wavelengths where a chemical species strongly radiates light. An absorption line spectrum is a wavelength range where a chemical species strongly absorbs light.

A variety of spectroscopic techniques are available. These techniques include visible and infrared light spectroscopy, ultraviolet light spectroscopy, and Raman spectroscopy. Raman spectroscopy involves atomic/molecular transitions that occur between different vibrational or rotational states.

BRIEF SUMMARY

While optical absorption spectra can provide signatures for identifying particular gases, the absorption spectra of a gas at low concentrations can be masked by background spectra of other gases. Also, the measurement of only a portion of absorption spectra may not suffice to identify a gas with a complex molecular structure.

A first aspect features a method for detecting or identifying a chemical analyte. The method includes measuring a nontrivial set of correlations between optical illumination wavelengths of a sample and emission wavelengths of the sample. The method includes comparing the measured set of correlations to a reference nontrivial set of correlations between optical illumination and emission wavelengths of a specific chemical analyte. The method also includes determining whether the specific chemical analyte is present in the sample based on a result of the comparing.

A second aspect features an apparatus. The apparatus includes a data processor and a light detector that is configured to measure optical emission spectra and to transmit data representative of the spectra to the processor. The data processor is configured to find a nontrivial set of correlations between optical illumination and emission wavelengths of the sample based on the transmitted data. The data processor is also configured to compare the found nontrivial set of correlations to a nontrivial reference set of correlations between optical illumination and emission wavelengths of a chemical analyte.

BRIEF DESCRIPTION OF THE DRAWINGS

In the Figures and text, like reference numerals indicate elements with similar functions.

In the Figures, the relative dimensions of some features may be exaggerated to more clearly illustrate one or more of the structures therein.

Herein, various embodiments are described more fully by the Figures and the Detailed Description of Illustrative Embodiments. Nevertheless, the inventions may be embodied in various forms and are not limited to the embodiments described in the Figures and Detailed Description of Illustrative Embodiments.

DETAILED DESCRIPTION OF ILLUSTRATIVE EMBODIMENTS

Figure 1:
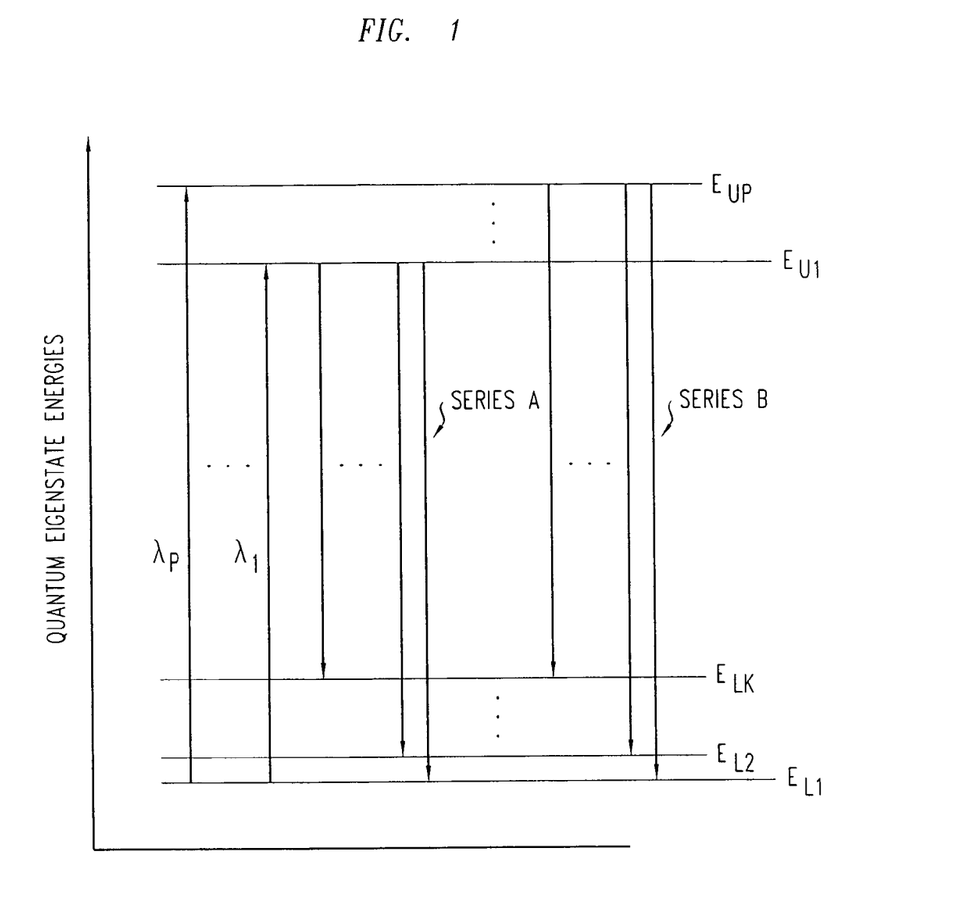
FIG. 1 qualitatively illustrates a possible set of quantized energy levels of an analyte and adsorption and emission transitions between said levels.

To aid in illustrating embodiments herein, a portion of a possible diagram of energy levels of an exemplary complex molecule is qualitatively illustrated in FIG. 1. The diagram includes lower energy levels $E_{L1}$, $E_{L2}$, ... $E_{Lk}$ and upper energy levels $E_{U1}$, ... $E_{Up}$ of the molecule. The energy levels $E_{L1}$-$E_{Lk}$ and $E_{U1}$-$E_{Up}$ are the energies of quantum eigenstates of Hamiltonian for the complex molecule. The complete set of such quantized energy levels will vary for different molecules. While the complete set of such quantized energy levels is an excellent identification fingerprint for many specific molecular analytes, it is typically difficult or impossible to measure the complete set of such quantized energy levels.

In various embodiments, the absorption of light of wavelengths $\lambda_1, \ldots, \lambda_p$ excites the complex molecule from one of its lower energy levels, $E_{L1}$, to its upper energy levels $E_{U1}$-$E_{Up}$. After such a light-induced excitation, a spontaneous relaxation causes the complex molecule to emit light belonging to an emission series, e.g., emission series A or emission series B. Each emission series is associated with one of the upper quantized energy levels $E_{U1}$-$E_{Up}$.

Herein, an emission means both a process where a molecule produces light that is coherent with respect to the illumination light that excited the molecule and a process where the molecule produces light that is incoherent with respect to the illumination light that excited the molecule. For example, an emission may involve producing light via an inelastic scattering off the molecule, i.e., known as Raman scattering.

The identification of a specific chemical analyte through observations of its emission series, e.g., A or B, may have two problems. First, the lines of the emission may be very faint and, thus difficult to accurately observe. Second, a single series may not be sufficiently distinct to identify a complex molecule. For example, a single series may indicate that such a complex molecule has a particular functional group, but may not indicate whether the molecule has another functional group on a distant portion of the molecule.

The negative impact of the above-described problems on detecting and/or identifying complex molecules may be reduced or circumvented by replacing simple observations of emission spectra by observations of the correlations between illumination and emission spectra. The use of such correlations to identify complex molecular analytes may be advantageous for two reasons.

First, different illumination wavelengths often produce different emission spectra. For example, FIGS. 2A and 2B qualitatively illustrate portions of possible emission spectra that molecules of a chemical analyte may produce when illuminated by input light whose wavelength, $\lambda_{IN}$, is given by $\lambda_A$ and $\lambda_B$, respectively. The two spectra may have emission peaks at different wavelengths, emission peaks of different size, and/or different numbers of emission peaks. For example, such different spectra may result due to the excitation of different functional groups on the molecules of the chemical analyte by the illumination light of wavelengths $\lambda_A$ and $\lambda_B$. For that reason, correlating emission spectra to illumination wavelength may provide more distinctive data for identifying a chemical analyte with a complex molecular structure.

Second, at some wavelengths, the illumination photons have energies that about equal to the difference between the energy of a selected excited energy level and the energy of a populated energy level of the molecule of a chemical analyte. Thus, illuminating such molecules with light of those wavelengths can resonantly excite the molecules to the selected excited energy levels, e.g., via a virtual process. Such virtual or real resonant excitation can very substantially increase the emission rate for one or more of the emission series that correspond to the selected excited state. Indeed, the emission rate may increase by one or more orders of magnitude when such a real or virtual resonant excitation of a molecule is produced. For that reason, the emission lines of that series may become much stronger than would otherwise be possible. Also, the emission lines of that series will be more strongly correlated to the illumination wavelength that caused such resonant excitation than with other illumination wavelengths.

Since Raman spectra may be weak and may provide data on limited portions of a complex molecule, correlations between illumination and emission wavelengths may be advantageous when the spectral fingerprints for detecting and/or identifying complex chemical analytes are based on Raman spectra.

Herein, a correlation is a relation between illumination wavelengths of a sample and wavelengths at which the sample emits light when exposed to light of the illumination wavelengths. A nontrivial set of correlations includes a set of wavelength pairs. In each pair, one member is an illumination wavelength and the other member is an emission wavelength that differs from the illumination wavelength of the same pair. The emission wavelength is a wavelength of a bright line in a spectrum of the sample that would be measured when the sample is illuminated by light of the illumination wavelength. A nontrivial set of correlations includes such wavelength pairs for a plurality of different illumination wavelengths and for a plurality of different emission wavelengths. In the wavelength pairs, the illumination wavelengths may be wavelengths at which light can resonantly excite molecules in the sample.

Figure 2A:
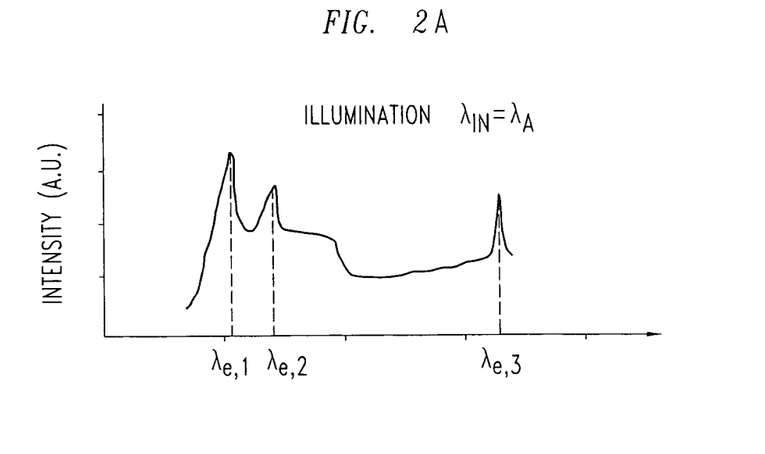
FIGS. 2A-2B qualitatively illustrate Raman emission spectra that may be produced by a chemical analyte when illuminated with first and second wavelengths of light.
Figure 2B:
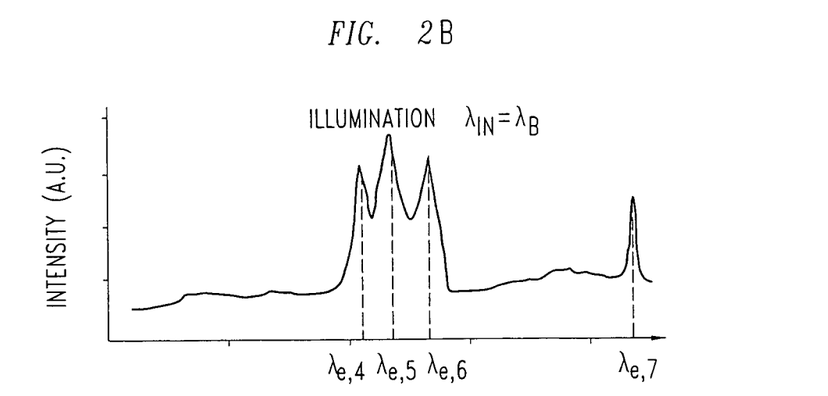

Examples of a nontrivial set of correlations can be derived from the emission spectra of FIGS. 2A and 2B. For a sample having those emission spectra, a nontrivial set of correlations may be formed, e.g., of the wavelength pairs $(\lambda_A, \lambda_{e,1})$, $(\lambda_A, \lambda_{e,2})$, $(\lambda_A, \lambda_{e,3})$, $(\lambda_B, \lambda_{e,4})$, $(\lambda_B, \lambda_{e,6})$ and $(\lambda_B, \lambda_{e,7})$. Such a set may provide a good fingerprint for identifying the sample.

Apparatus for optically detecting and/or identifying chemical analyte(s) by measuring correlations between absorption and emission wavelengths may use a variety of geometries to deliver illumination light to a sample and to receive emitted light from the sample. Such an apparatus may be configured to use a forward, backward, or side geometry for collecting emission light for measuring the types of absorption and emission correlations described above. Exemplary embodiments of apparatus with such configurations are illustrated in FIGS. 3A-3C.

Figure 3A:
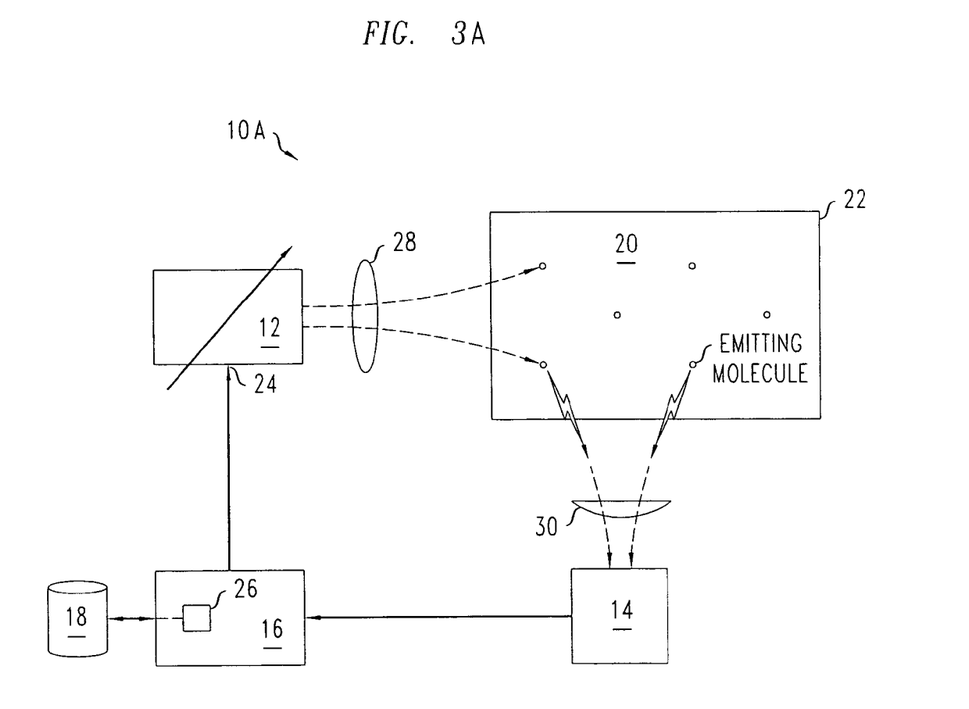
FIG. 3A is a block diagram schematically illustrating an embodiment of an apparatus for detecting the presence of or identifying a chemical analyte in a sample.
Figure 3B:
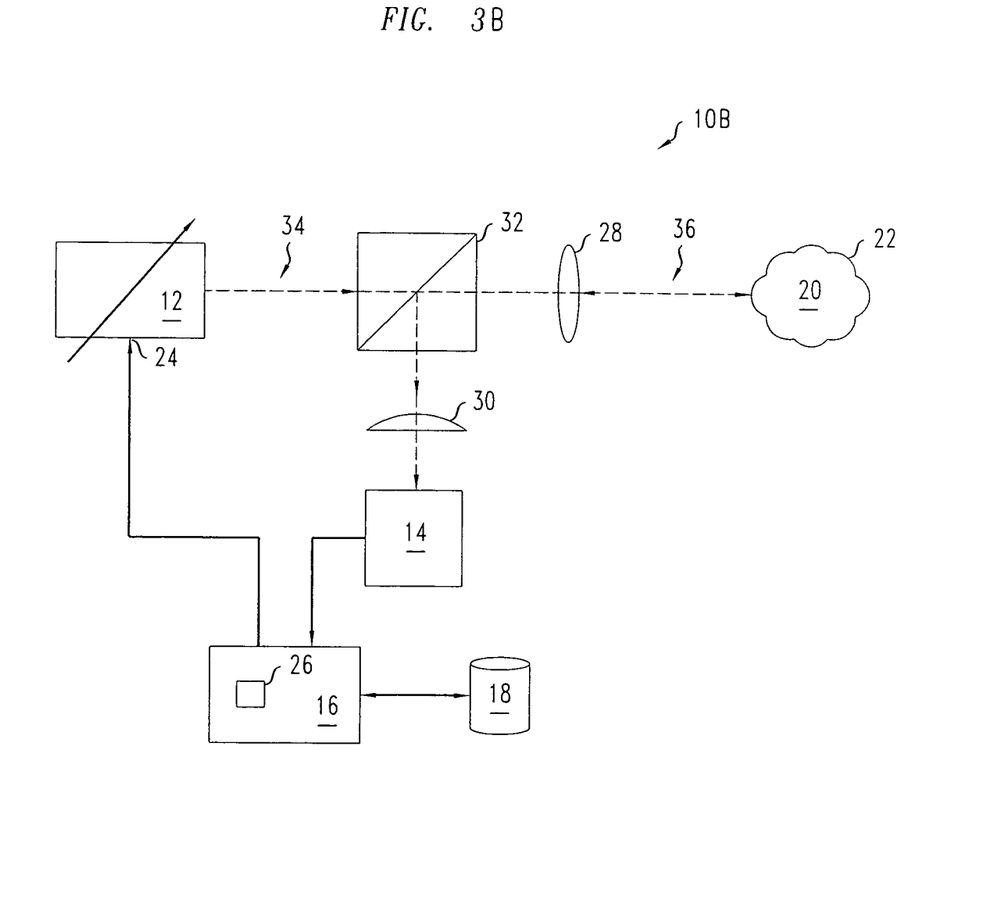
FIG. 3B is a block diagram schematically illustrating another embodiment of an apparatus for detecting the presence of or identifying a chemical analyte in a sample.
Figure 3C:
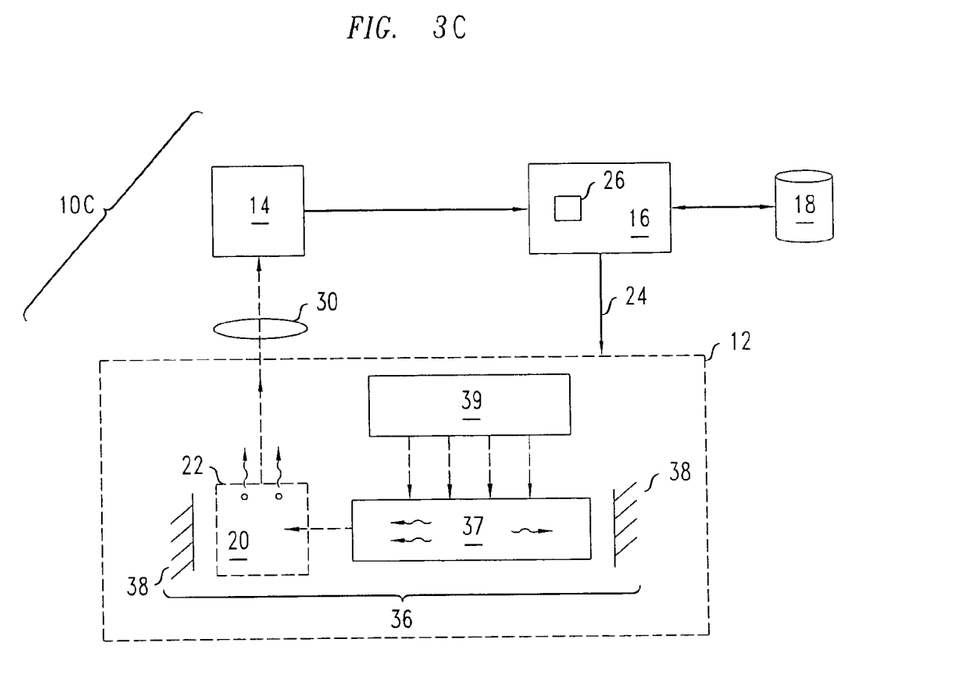
FIG. 3C is a block diagram schematically illustrating another embodiment of a apparatus for detecting the presence of or identifying a chemical analyte in a sample.

FIGS. 3A, 3B, and 3C illustrates apparatus 10A, 10B, and 10C, which measure a nontrivial set of correlations between a sample's optical absorption and emission wavelengths to detect or identify one or more chemical analytes therein. Each apparatus 10A, 10B, 10C includes a wavelength-tunable light source 12, a light detector 14, a data processor 16, and a digital data storage apparatus 18.

The wavelength-tunable light source 12 produces or emits substantially monochromatic light in a range of wavelengths that are absorbed or scattered inelastically by a sample 20 located in a sample region 22. An exemplary light-source 12 is a conventional wavelength-tunable laser. The light source 12 may be controllable to temporally sweep a range of wavelengths in a manner that is responsive to control signals received at an electrical control input 24.

The light detector 14 is configured to receive light emitted from sample 20, which is located in the sample region 22. The received light may emitted or scattered in a forward, a side, or a backwards direction with respect to the propagation direction of the illumination light from the light source 12. For example, FIGS. 3A and 3C illustrate apparatus 10A, 10C in which the light detector 14 may detect side-emitted light, and FIG. 3B illustrates an apparatus 10C in which the light detector 14 detects backwards emitted and/or scattered light.

The light detector 14 is configured to measure an intensity spectrum of the light emitted and/or scattered by the sample 20. That is, the light detector 14 measures light intensity as a function of wavelength in one or more series of consecutive wavelength bins. The light detector 14 may be a Raman spectrometer that is specifically configured to measure Raman spectra. For example, the light detector 14 may include a dispersive element such as an optical grating and a spatially segmented light intensity detector such as a charge-coupled detector (CCD) or an exit slit where the dispersive element and spatially segmented light intensity detector are positioned to enable the measurement of a light spectrum. In some embodiments, the light detector 14 may be a multichannel detector that can perform parallel measurements of light intensities in one or more sequences of consecutive wavelength bins. Such multichannel detectors may simplify or increase the speed of the measurement of data needed to determine correlations between illumination and absorption wavelengths.

The data processor 16 is connected to receive from the light detector 14 data representative of intensity spectra measured therein and may be connected to receive data representative of the illumination wavelengths produced by the light source 12. For example, the data processor 18 may receive measured spectral intensities and corresponding wavelengths from the light detector 14. The data processor 16 is configured and/or programmed to use such received data to find a nontrivial set of correlations between absorption and emission wavelengths of the sample 20, i.e., based on spectral measurements and to detect the presence of or identify one or more chemical analytes in the sample 20 based on the found nontrivial set of correlations.

The data processor 16 includes a digital data processor 26. The digital data processor 26 may be connected to one or more internal or external digital data storage apparatus 18 by one or more data buses. The digital data storage apparatus 18 may include a random access memory, a read only memory and/or an optical or magnetic disk reader and magnetic or optical disk inserted therein. The data processor 16 and digital data storage apparatus 18 may be in a conventional programmed computer.

The digital data storage apparatus 18 may store program(s) for operating the apparatus 10A-10C and/or may store fingerprint sets of absorption and emission wavelength correlations for selected chemical analytes. For example, the data processor 16 may use such sets for comparing to measured correlations so that the data processor 16 can determine whether one or more chemical preselected analytes are present in the sample 20.

The one or more data storage apparatus 18 may be encoded with one or more computer-executable programs of instructions. One of the programs may encode a method of detecting and/or identifying chemical analyte(s). One or more of the programs may encode a method for controlling the light source 12 and/or receiving the data representative o the measured intensity spectra from the light detector 14.

The sample 20 may include one or more chemical analytes whose detection and/or identification via the apparatus 10A-10C is desirable. Such chemical analyte(s) may include explosive compounds, e.g., tri-nitro toluene (TNT), dangerous chemicals, e.g., hydrogen sulfide, and/or other compounds whose detection or identification is desired. The one or more chemical analytes may be gaseous, solid, liquid, or solvated or suspended in another medium.

In some embodiments, the apparatus 10 may also include bulk optical components 28, 30. The optical component 28 may filter, focus and/or defocus light from the light source 12 to appropriately illuminate sample 20. The optical component 30 may filter and/or focus light emitted or scattered by the sample 20 onto the light detector 14. In light of the above disclosure, one of skill in the art would know how to make and use optical components 28, 30.

Referring to FIG. 3B, the apparatus 10B is configured to detect or identify chemical analyte(s) in a sample 20 that is located in a distant sample region 22. The apparatus 10B includes an optical beam splitter 32 so that illumination light beam 34 and light emitted or scattered by the sample 20 may follow a single optical path 35. In particular, the illumination light 34 may be directed by optical component 28, e.g., a telescopic lens system, onto a specifically targeted distant sample 20, and the same optical component 28 may receive light backscattered and/or emitted by the sample 20. A portion of such a received light may then, be directed by optical beam splitter 32 towards the optional optical component 30 and towards the light detector 14.

In some embodiments, the apparatus 10B may combine a laser imaging detection and ranging (LIDAR) system and a detector of chemical analyte(s). In such embodiments, the source 12 may generate illumination light for both LIDAR and chemical analyte detection. Then, the estimation of the distance and/or speed of the sample 20 and the detection and/or identification of chemical analyte(s) in the sample 20 may be based on backscattered and/or back emitted light, wherein said light is directed to the light detector 14 via the optical beam splitter 32 and optionally via the optical component 30. The data processor 16 may analyze light spectra measured by the light detector 14 to determine both distance/movement and analyte composition information on the specifically targeted distant sample 20.

Referring to FIG. 3C, the apparatus 10C is configured to detect or identify one or more chemical analytes in a sample 22 located in a laser cavity 36 of a laser illumination source 12. The laser cavity 36 includes a volume of material 37 and reflectors 38 that close opposite ends of the laser cavity 36. The volume of material 37 emits light in response to being optically or electrically pumped by a laser pump source 39 thereby producing the laser light. For example, the volume of material 37 may include dye molecules so that the laser source 12 is a wavelength-tunable dye laser. The laser cavity 36 also includes the sample 20 in a portion thereof. Thus, the sample 20 may be subjected to high light densities due to stimulated emission of photons (e.g., indicated by wiggly lines) in the laser cavity 36. Indeed, the interior of the laser cavity may provide very high illumination intensity, which is advantageous for measuring weak Raman emission spectra for use in determining corresponding optical absorption and emission correlations of the sample 20.

For complex and/or rarified chemical analytes, simple light absorption spectra or ordinary Raman emission spectra may not be convenient fingerprints for unambiguously detecting or identifying the chemical analytes. In particular, a measured Raman emission spectrum may not be an unambiguous fingerprint for a complex chemical analyte. Also, a generic Raman emission spectrum may have very low intensity lines thereby making its measurement susceptible to large errors and/or large technical difficulties. For the above reasons, a measured nontrivial set of correlations between absorption wavelengths and Raman emission spectra may provide a better fingerprint for detecting or identifying the chemical analytes via Raman spectroscopy.

Figure 4:
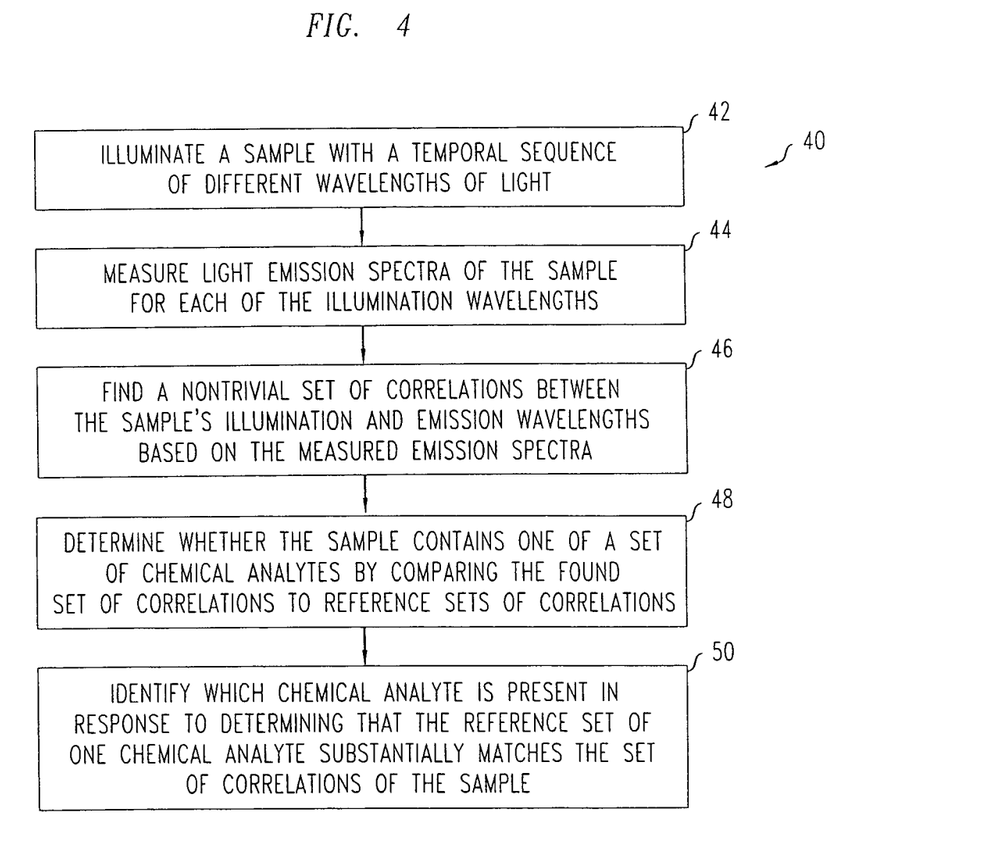
FIG. 4 is a flow chart illustrating a method for detecting and/or identifying a chemical analyte in a sample, e.g., with one of the apparatus of FIGS. 3A-3C.

FIG. 4 illustrates a method 40 for detecting and/or identifying a chemical analyte through the measurement of a nontrivial set of correlations between the light absorption and emission wavelengths of a sample, e.g., as described in the preceding paragraph. The method 40 may be performed, e.g., to operate embodiments of any of the apparatus 10A-10C illustrated in FIGS. 3A-3C.

The method 40 includes illuminating a sample that may contain one or more chemical analytes with a temporal sequence of different wavelengths of substantially monochromatic light (step 42). For example, the illuminating step may include temporally sweeping the output wavelength of a wavelength-tunable laser, e.g., one of the light sources 12 of FIG. 3A-3C, so that a selected sample, e.g., the sample 20 of FIGS. 3A-3C, is swept by light of a sequence of wavelengths.

The method 40 includes measuring one or more spectra of light emitted by the sample for each illumination wavelength of the sequence at step 42 (step 44). The measuring step 40 may involve determining wavelengths for a plurality of emission peaks of the sample for the illumination wavelengths of the sequence of step 42. The emission peaks may be measured, e.g., by the light detector 14 of FIG. 3A-3C. The wavelength of each measured emission peak differs from the corresponding wavelength of the illumination light that caused the sample to emit light.

The method 40 includes finding or measuring a nontrivial set of correlations between the sample's absorption and emission wavelengths based on the illumination wavelengths applied to the sample at above step 42 and the corresponding emission spectra that were measured at above step 44 (step 46). The found nontrivial set of correlations may include a proper subset of the sample illumination wavelengths of step 42 and for each wavelength of said proper subset, the wavelengths of a group of emission peaks in the spectra produced by the sample in response to being subjected to light of the corresponding illumination wavelength. The intensity peaks may correspond, e.g., to peaks in a Raman emission spectrum of the sample.

The method 40 includes determining whether the sample contains one of a selected set of chemical analytes by comparing the nontrivial set of correlations that were found or measured at step 46 to one or more reference nontrivial sets of such correlations (step 48). The determining step 48 includes finding that a particular chemical analyte is present in the sample in response to determining that one of the reference nontrivial sets of correlations substantially matches the nontrivial set of correlations found or measured at step 46 and may include determining that the particular chemical analyte is otherwise, absent from the sample. Here, each reference set of correlations is a nontrivial set of correlations for one particular chemical analyte, e.g., as measured during a calibration step of the apparatus 10A-10C. Two sets of correlations substantially match if a plurality of the pairs of corresponding absorption and emission wavelengths therein match between the two sets of correlations and said matches occur for a plurality of the absorption wavelengths.

In various embodiments, the steps 46 and 48 of the method 40 may be performed by the processor 16 of FIG. 3A-3C. In some such embodiments, the one or more reference sets of correlations, i.e., of reference chemical analytes, are stored on the data storage apparatus 18 and are accessed by the processor 16 during the performance of the step 46 and/or step 48.

In some embodiments, the emission wavelengths of the correlations found at step 46 and the emission wavelengths of the reference sets of correlations correspond to Raman emission spectral lines. In some embodiments of the method 40, the Raman emission spectra may correspond to rotational spectra of selected chemical analyte(s) whose detection or identification are desired.

In some embodiments, the method 40 also includes identifying a specific chemical analyte as being present in the sample in response to the reference nontrivial set of correlations of the specific chemical analyte substantially matching the found or measure nontrivial set of correlations of the sample as obtained at the step 46 (step 50).

In some embodiments, some or all of the steps 42-50 of the method 40 are encoded as instructions on the data storage apparatus 18 of FIG. 3A-3C in a form that is executable by the digital data processor 26 of FIGS. 3A-3C.

From the disclosure, drawings, and claims, other embodiments of the invention will be apparent to those skilled in the art.

What is claimed is:

1. An apparatus, comprising:
   a data processor;
   a light detector configured to measure optical emission spectra of a sample and to transmit data representative of the measured emission spectra to the processor; and
   wherein the data processor is configured to find a nontrivial set of correlations between optical illumination and emission wavelengths of the sample based on the transmitted data; and
   wherein the data processor is configured to compare the found nontrivial set of correlations to a nontrivial reference set of correlations between optical illumination and emission wavelengths of a chemical analyte.

2. The apparatus of claim 1, wherein the data processor is configured to determine that the chemical analyte is present in the sample in response to determining that the found and reference nontrivial sets of correlations substantially matching.

3. The apparatus of claim 1, wherein the data processor is configured to determine that the chemical analyte is absent from the sample in response to determining that the found and reference nontrivial sets of correlations do not substantially match.

4. The apparatus of claim 1, further comprising:
   a light source configured to illuminate the sample with light at a temporal sequence of wavelengths;
   a light detector configured to measure an emission spectrum of the sample at each illumination wavelength of the sequence; and
   wherein the processor is configured to find the nontrivial set of correlations based on a proper subset of the illumination wavelengths of the temporal sequence, the proper subset including a plurality of illumination wavelengths.

5. The apparatus of claim 4, wherein the processor is configured to find the nontrivial set of correlations based on Raman spectra of the sample.

6. The apparatus of claim 4, wherein the detector is a multichannel light detector.

7. The apparatus of claim 4, wherein the source includes a laser cavity configured to illuminate a sample located therein and the light detector is configured to detect light emitted by the sample located in the laser cavity.

8. The apparatus of claim 4,
   wherein the source is configured to illuminate a remotely located sample with a beam of the illumination light and
   wherein the light detector is configured to detect light emitted from the remotely located sample towards the source.

* * * * *